United States Patent [19]
First et al.

[11] Patent Number: 5,840,549
[45] Date of Patent: *Nov. 24, 1998

[54] MALE INFERTILITY Y-DELETION DETECTION BATTERY

[75] Inventors: Marijo Kent First; Ariege Muallem, both of Madison, Wis.

[73] Assignee: Promega Corporation, Madison, Wis.

[ * ] Notice: The term of this patent shall not extend beyond the expiration date of Pat. Nos. 5,776,682 and 5,783,390.

[21] Appl. No.: 753,979

[22] Filed: Dec. 4, 1996

Related U.S. Application Data

[63] Continuation-in-part of Ser. No. 531,556, Sep. 18, 1995, which is a continuation-in-part of Ser. No. 472,416, Jun. 7, 1995.

[51] Int. Cl.$^6$ .............................. C12P 19/34; C07H 21/04; C12N 15/00
[52] U.S. Cl. ...................... 435/91.2; 435/810; 536/24.33; 536/25.3; 935/8; 935/77; 935/78
[58] Field of Search .............................. 435/6, 91.1, 91.2, 435/183, 810; 536/23.1, 24.3, 24.33, 25.3; 935/8, 72, 78

[56] References Cited

FOREIGN PATENT DOCUMENTS

WO87/05027  8/1987  WIPO .
WO89/02440  3/1989  WIPO .

OTHER PUBLICATIONS

Affara, N.A., Lau, Y.–F.C., Briggs, H., Davey, P., Jones, M.H., Khwaja, O., Mitchell, M., and Sargent, C. (1994) *Report of the First International Workshop on Human Y Chromosome Mapping 1994*. Cytogenet Cell Genet 67, 359–402.

Agulnik, A.I., Mitchell, M.J., Lerner, J.L., Woods, D.R., and Bishop, C.E. (1994) *A mouse Y chromosome gene encoded by a region essential for spermatogenesis and expression of male–specific minor histocompatibility antigens.* H. Mol. Gen. 3, 873–878.

Chandley, A.C. and Cooke, H.J. (1994) *Human male fertility–Y–linked genes and spermatogenesis.* H. Mol. Gen. 3, 1449–1452.

Henegariu, O., Hirschmann, P., Kilian, K., Kirsch, S., Lengauet, C., Maiwald, R., Mielke, K., and Vogt, P. (1994) *Rapid screening of the Y chromosome in idiopathic sterile men, diagnostic for deletions in AZF, a genetic Y factor expressed during spermatogenesis.* Andrologia 26, 97–106.

Kobayashi, K., Mizuno, K., Hida, A., Komaki, R., Tomita, K., Matsishita, I., Namiki, M., Iwamoto, T., Tamura, S., Minowada, S., Nakahori, Y., and Nakagome, Y. (1994) *PCR analysis of the Y chromosome long arm in azoospermic patients: evidence for a second locus required for spermatogenesis.* H. Mol. Gen. 3, 1965–1967.

Ma, K., Sharkey, A., Kirsch, S., Vogt, P., Keil, R., Hargreave, T.B., McBeath, S., and Chandley, A.C. (1992) *Towards the molecular localisation of the AZF locus: mapping of microdeletions in azoospermic men within 14 subintervals of interval 6 of the human Y chromosome*, H. Mol. Gen. 1, 29–33.

Ma, K., Inglis, J.D., Sharkey, A., Bickmore, W.A., Hill, R.E., Prosser, E.J., Speed, R.M., Thomson, E.J., Jobling, M., Taylor, K., Wolfe, J., Cooke, H.J., Hargreave, T.B., and Chandley, A.C., (1993) *A Y Chromosome Gene Family with RNA–Binding Protein Homology: Candidates for the Azoospermia Factor AZF Controlling Human Spermatogenesis.* Cell 75, 1287–1295.

Nagafuchi, S., Namiki, M., Nakahori, Y., Kindoh, N., Okuyama, A., and Nakagome, Y. (1993) *A Minute Deletion Of The Y Chromosome In Men With Azoospermia.* The J. of Urol. 150, 1155–1157.

Sommer and Tautz, "Minimal homology requirements for PCR primers," Nucleic Acids Research, vol. 17, No. 16, p. 6749, 1989.

*Primary Examiner*—Bradley L. Sisson
*Attorney, Agent, or Firm*—DeWitt Ross & Stevens SC

[57] ABSTRACT

The present disclosure discloses a method for probing the integrity of a Y chromosome utilizing multiplex PCR reactions which amplify specific regions of the human Y chromosome which have been linked to normal fertility in human males. The method is capable of detecting deletion mutations within the Y chromosome which are predictive of human male infertility. A kit containing reagents needed to practice the method is also disclosed.

21 Claims, 1 Drawing Sheet

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTTAGGAAAA AGTGAAGCCG      20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CCTGCTGTCA GCAAGATACA      20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (i i) MOLECULE TYPE: DNA (genomic)

(x i) SEQUENCE DESCRIPTION: SEQ ID NO:3:

AGGCACTGGT CAGAATGAAG                                                                 20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:4:

AATGGAAAAT ACAGCTCCCC                                                                 20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:5:

AGAGAGTTTT CTAACAGGGC G                                                               21

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:6:

TGGGAATCAC TTTTGCAACT                                                                 20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:7:

TCAGAAGTGA AACCCTGTAT G                                                               21

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:8:

GCATGTGACT CAAAGTATAA GC 22

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CGGGGAGGAG ACAGAGGGGG TAGG 24

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTGAGAAGGG GCGGGGCGTG TA 22

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATTTTGCCTT GCATTGCTAG 20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TTTTTAAGCC TGTGACCTGG 20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCAGTTCCAT TGTTTGCTTC 20

(2) INFORMATION FOR SEQ ID NO:14:

( i ) SEQUENCE CHARACTERISTICS:
: ( A ) LENGTH: 25 base pairs
: ( B ) TYPE: nucleic acid
: ( C ) STRANDEDNESS: single
: ( D ) TOPOLOGY: linear ( i i ) MOLECULE TYPE: DNA (genomic)

( x i ) SEQUENCE DESCRIPTION: SEQ ID NO:14:

GCAGCATAAT AGCTATACAG TATGG 25

( 2 ) INFORMATION FOR SEQ ID NO:15:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: DNA (genomic)

( x i ) SEQUENCE DESCRIPTION: SEQ ID NO:15:

TACGGGTCTC GAATGGAATA 20

( 2 ) INFORMATION FOR SEQ ID NO:16:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: DNA (genomic)

( x i ) SEQUENCE DESCRIPTION: SEQ ID NO:16:

TCATTGCATT CCTTTCCATT 20

( 2 ) INFORMATION FOR SEQ ID NO:17:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: DNA (genomic)

( x i ) SEQUENCE DESCRIPTION: SEQ ID NO:17:

AGCTTCTATT CGAGGGCTTC 20

( 2 ) INFORMATION FOR SEQ ID NO:18:

( i ) SEQUENCE CHARACTERISTICS:
: ( A ) LENGTH: 20 base pairs
: ( B ) TYPE: nucleic acid
: ( C ) STRANDEDNESS: single
: ( D ) TOPOLOGY: linear ( i i ) MOLECULE TYPE: DNA (genomic)

( x i ) SEQUENCE DESCRIPTION: SEQ ID NO:18:

CTCTCTGCAA TCCCTGACAT 20

( 2 ) INFORMATION FOR SEQ ID NO:19:

( i ) SEQUENCE CHARACTERISTICS:
: ( A ) LENGTH: 20 base pairs
: ( B ) TYPE: nucleic acid
: ( C ) STRANDEDNESS: single ( D ) TOPOLOGY: linear ( i i ) MOLECULE TYPE: DNA (genomic)

( x i ) SEQUENCE DESCRIPTION: SEQ ID NO:19:

ATTGATGTGT TGCCCCAAAT                                                                    20

( 2 ) INFORMATION FOR SEQ ID NO:20:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:20:

AGAGTGAACT TTAAATCCCA GCC                                                                23

( 2 ) INFORMATION FOR SEQ ID NO:21:

( i ) SEQUENCE CHARACTERISTICS:
          ( A ) LENGTH: 29 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:21:

ACAGTTTGAA ATGAAATTTT AAATGTGTT                                                          29

( 2 ) INFORMATION FOR SEQ ID NO:22:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:22:

TGACAAAGTG AGACCCTACT ACTA                                                               24

( 2 ) INFORMATION FOR SEQ ID NO:23:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:23:

CGGGGAGGAG ACAGAGGGGG TAGG                                                               24

( 2 ) INFORMATION FOR SEQ ID NO:24:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:24:

CTGAGAAGGG GCGGGGCGTG TA 22

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GTGGTCTGTG GAAGGTGTCA 20

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CCTCCAGACC TGGACAGAAT T 21

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

AAAAATGAGT GGCACTATGT ACA 23

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

CTGCAGGCAG TAATAAGGGA 20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GGGAGAGTCA CATCACTTGG 20

( 2 ) INFORMATION FOR SEQ ID NO:30:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:30:

TTGAATTATC TGCCTGAGTG C 21

( 2 ) INFORMATION FOR SEQ ID NO:31:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:31:

GAGAGTCATA ATGCCGACGT 20

( 2 ) INFORMATION FOR SEQ ID NO:32:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:32:

TGGTCTCAGG AAGTTTTTGC 20

( 2 ) INFORMATION FOR SEQ ID NO:33:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

GCATCCTCAT TTTATGTCCA 20

( 2 ) INFORMATION FOR SEQ ID NO:34:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:34:

CAACCCAAAA GCACTGAGTA 20

( 2 ) INFORMATION FOR SEQ ID NO:35:

( i ) SEQUENCE CHARACTERISTICS:
    ( A ) LENGTH: 21 base pairs
    ( B ) TYPE: nucleic acid
    ( C ) STRANDEDNESS: single (D) TOPOLOGY: linear (i i) MOLECULE TYPE: DNA (genomic)

(x i) SEQUENCE DESCRIPTION: SEQ ID NO:35:

AAGACAGTCT GCCATGTTTC A                                            21

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:36:

ACAGGAGGGT ACTTAGCAGT                                              20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:37:

CAGGCAGGAC AGCTTAAAAG                                              20

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:38:

ACTGTGGCAA AGTTGCTTTC                                              20

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:39:

CGGGGAGGAG ACAGAGGGGG TAGG                                         24

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued ( i i ) MOLECULE TYPE: DNA (genomic)

( x i ) SEQUENCE DESCRIPTION: SEQ ID NO:40:

CTGAGAAGGG GCGGGGCGTG TA                          22

MALE INFERTILITY Y-DELETION DETECTION BATTERY

This is a Continuation-In-Part of application Ser. No. 08/531,556, filed Sep. 18, 1995, which is a Continuation-in-Part of application Ser. No. 08/472,416, filed Jun. 7, 1995.

FIELD OF THE INVENTION

The present invention relates to detection of deletion mutations in the Y chromosome of human males. More specifically, the present invention relates to a multiplex polymerase chain reaction (PCR) assay for the detection of Y chromosome deletion mutations which are indicative of male infertility.

BIBLIOGRAPHIC CITATIONS

Complete bibliographic citations to the references discussed herein are contained in the Bibliography section, directly preceding the Sequence Listing.

DESCRIPTION OF THE PRIOR ART

Starting in 1905, when Netti Stevens and Edmund Wilson independently described the first direct evidence to support the chromosomal theory of sex determination, researchers have been studying the sex chromosomes to determine the other traits which are controlled by the expression of products encoded on the X and Y chromosomes. For instance, shortly after Stevens' and Wilson's experiments, Thomas Hunt Morgan showed that the white-eyed mutation in Drosophila is a sex-linked recessive trait localized to the X chromosome. More recently, with the advent of far more powerful gene mapping tools, many researchers have investigated the Y chromosome to determine those loci responsible for male gonadal development in newborns, and fertility in adult human males.

Of particular interest is the determination of a cause for infertility in those couples where no apparent etiology can be ascribed. It is generally believed that world wide between 2 and 8 percent of all couples are infertile. Not unexpectedly, the apparent cause of 50% of the couples experiencing difficulty having children can be traced to infertility in the male. Etiology of some of these cases of infertility can be identified by microscopic examination of the ejaculate from the male. In this manner, obvious causes of male infertility, such as no sperm in the ejaculate (azoospermia), reduced number of sperm (oligospermia), or sperm having abnormal morphology (e.g. asthenozoospermia and teratospermia) are identified. However, between 30 to 50 percent of the cases of male infertility are categorized as being idiopathic, that is, of unknown origin and having no microscopically obvious cause. This large number of infertility cases of unknown origin, and the devastating effect these have on the infertile couples has created a strong desire on the part of various researchers to obtain a better understanding of the causes of infertility in general, and on the identification of genetic factors which are associated with male infertility in particular.

To that end, many researchers are presently studying deletion mutations on the Y chromosome in azoospermic and oligospermic men. It is hoped that such studies will reveal the genetic basis for many cases of infertility now designated idiopathic. The following references all describe genetic studies of the Y chromosome in an effort to delineate those gene loci required for spermatogenesis and normal male fertility.

Two Patent Cooperation Treaty applications filed by David C. Page of the Whitehead Institute for Biomedical Research describe Y-specific DNA which can be used as probes to establish unambiguously the presence or absence of regions of the normal Y chromosome. (PCT Serial Number WO 87/05027, published 27 Aug. 1987; and PCT Serial Number WO 89/02440, published 23 Mar. 1989.) Both of these references note a prevailing problem in analyzing the Y chromosome: Because the Y chromosome normally appears only in the haploid state, it has very little opportunity to recombine with a homolog. This makes genetic linkage studies of the Y chromosome extremely difficult, if not impossible, using conventional linkage techniques. Page also notes that attempts to establish the Y-linkage of certain traits have been inconclusive because of the difficulty in distinguishing true Y-linked inheritance from sex-limited expression of proteins encoded on the Y chromosome.

However, using cytogenetic techniques such as karyotyping and staining, there is evidence that a number of genes in addition to those required for sex determination lie on the Y chromosome. The Page patent applications describe a method to circumvent the difficulties of mapping genes to the Y chromosome by probing the genetic makeup of a test subject with probes consisting of restriction fragments of the Y chromosome from normal subjects. Using the Y-DNA probes, Page constructed a deletion map of the human Y chromosome which can be used for comparison with deletion maps constructed using the same probes in individuals with abnormal karyotypes, or, as judged by cytogenetics, to have a structurally abnormal Y chromosome.

In short, Page describes the use of his deletion map of the normal Y chromosome as the basis for selecting and cloning Y-specific DNA restriction fragments described in his PCT applications to probe the DNA of a test subject for Y-chromosome deletions. In the earlier of the Page applications, the DNA fragments are described only in terms of molecular weight and presence of restriction enzyme cleavage sites. No base pair sequences are described. The later Page application includes a single DNA nucleotide sequence of a 1.2 kb Hind III fragment from a 135 kb region of the Y chromosome. The Page references describe using the probes to map the testis determining factor (TDF) to the short arm (Yp) of the Y chromosome.

The majority of the Y-DNA sequences used as hybridization probes by Page were derived from a library made from flow-sorted Y chromosomes obtained from the National Laboratory Gene Library Project. The library consisted of a lambda phage (Charon 21A) into which fragments of Y-chromosomal DNA (obtained by complete digestion of the DNA) had been cloned. Analysis of randomly selected Y-DNA-containing clones resulted in definition of deletion intervals along the Y chromosome. DNA sequences of interest were then removed from the lambda phage and recloned into a plasmid vector (e.g., pUC8 or pUC13).

Ma et al. (1992) used a similar approach to analyze structural abnormalities in the long arm of the Y chromosome (Yq) by genomic blot hybridization. Previous cytogenetic investigations in sterile men had suggested that the location of a gene controlling spermatogenesis, called the azoospermia factor (AZF), was in band q11.23 of the Y chromosome. Furthermore, molecular mapping had localized AZF to interval 6 of the Y chromosome. Using a series of 30 DNA probes previously mapped to Yq, Ma et al. found evidence for microdeletions in interval 6 in some azoospermic men.

Using the 30 probes, Ma et al. constructed a detailed deletion map of interval 6 of the human Y chromosome. Ma et al. differentiated interval 6 into 14 sub-intervals by probing genomic blots from 21 individuals with cytogenetically-defined deletions or rearrangements on the long arm of the Y chromosome. Using the results of the 21 blots, Ma et al. were able to map the DNA probes into 14 sub-intervals of interval 6, and to order the breakpoints of the patients' altered Y chromosome unambiguously.

A further paper by Ma et al. (1993), reports the isolation and characterization of a gene family located within a Y-chromosome deletion at interval 6, sub-interval XII–XIV. Using cosmid clones isolated from Y-specific probes which map to a distal interval deletion, Ma et al. identified a potential CpG island, an indication of the presence of a gene. Using DNA sequences from a testis cDNA library isolated using the cosmid, Ma et al. found that the sequences map only to the long-arm distal euchromatin.

Ma et al. (1993) conclude that the interval 6, sub-interval XII–XIV constitutes an excellent candidate for the AZF locus. In support of this conclusion, the reference notes that partial cDNA clones map to the distal deletion interval of Yq interval 6, a region associated with azoospermia. Additionally, the expression of the genes appears to be testis specific. Ma et al. were unable to detect expression in any other tissue. Lastly, Ma et al. note that at least part of one of the genes was contained within a microdeletion of 2 oligospermic patients. The genes also show a male-specific conservation in DNA from several other mammals.

References by Nagafuchi et al. (1993), and Kobayashi et al. (1994) describe deletion analysis of the Y chromosome in men with azoospermia. In the first reference, Nagafuchi et al. analyzed the Y chromosome DNA from 50 Japanese men with idiopathic azoospermia whose Y chromosomes were cytogenetically normal. Nagafuchi et al. used 17 Y-specific DNA fragments to probe the detection of 23 loci on the Y chromosome. Additionally, they used PCR to analyze 3 additional loci, including the SRY locus. Of the 50 subjects tested, 6 had small interstitial deletions which were located within the distal portion of Yq11. Of these 6 patients, 5 lacked the same 2 loci, DYS7C and DYS1. The remaining subject displayed a larger deletion which included the DYS7C locus, but not the DYS1 locus. The authors of this reference therefore presume that the proximal part of the Yq11 interval of the Y chromosome likely encompasses the gene deletion that causes azoospermia.

A further PCR analysis of the Y chromosome by Kobayashi et al. (1994) provides evidence that a second locus is necessary for spermatogenesis. Here, 63 Japanese azoospermic or severely oligospermic men without any apparent deletion in the Y chromosome, or cell line mosaicism, were examined for the presence or absence of a total of 16 loci including 15 loci between DYS7E and DYZ1 on Yq, and the YRRM locus. With the exception of the primer sequence for YRRM1, which was modified slightly from the Ma et al. reference described immediately above, Kobayashi et al. used the same primer pairs described by Ma et al.

Chandley and Cooke (1994) describe the isolation of the Y-located RNA recognition motif genes (YRRM). This review article notes that a feature of the YRRM domain is a pair of very highly conserved motifs. This reference also notes that the YRRM gene family has at least 15 members, and that transcription of the YRRM genes has not been detected outside the testis.

Henegariu et al. (1994) describe a multiplex PCR program for detecting deletions in the long arm of the human Y chromosome in Yq11. The PCR program is designed to quickly detect small interstitial deletions in this region of the Y chromosome. Henegariu et al. begin by noting that the genetic map created by Ma et al. (above), referred to as the "Ma map," was created using two small interstitial deletions in the proximal and distal portions of Yq11. Henegariu et al. note that because these micro deletions do not overlap, a question remains as to whether the genetically-defined AZF is represented by more than one spermatogenesis gene or by a very large gene structure.

Henegariu et al. constructed five multiplex PCR experiments using 28 Yq11-specific primer pairs. The combination of primer pairs for the five multiplex PCR experiments were selected such that the difference in length between any two amplification products in a mixture should be at least 18 to 20 bp. At this length, the amplification products will separate cleanly on a normal agarose gel matrix. Additionally, in order to prevent false positives for deletions due to experimental artifacts, the primers in one mix do not recognize two juxtaposed loci on the Y chromosome. Lastly, each mixture contains primer pairs from both the proximal and distal ends of the Yq11 interval. In this manner, each multiplex mixture will have at least 1 positive internal control in the event of a larger deletion event.

The five multiplex PCR mixtures are combined in separate tubes along with the necessary reactants to form a "PCR reaction cocktail." Conventional ingredients include sterile ultrafiltered water, buffer, salt, dNTP nucleotides, and Taq DNA polymerase. The solutions are then refrigerated or frozen until use.

To run the multiplex PCR analysis, five tubes are filled with the primer mixtures I–V, respectively. An aliquot of genomic DNA from the test subject is then introduced into each of the five tubes. The tubes are then placed directly in a thermocycler preheated to 94° C. The optimal cycling conditions for 50 cycles were found to be 94° C. for 30 seconds (melting); 54° C. for 45 seconds (annealing); and 65° C. for 120 seconds (extension). The PCR reaction products are then separated on agarose gels in a known manner.

In the event of a deletion of one or more of the PCR fragments, the deletion can be confirmed by analyzing the DNA of the test subject against a single primer pair PCR experiment using the primer pair deleted from the multiplex PCR reaction. A positive PCR primer pair may be added as an internal control. If the deletion of a given PCR product is only seen in the multiplex PCR experiment, but not in the single PCR experiment, its occurrence is most likely an artifact of the PCR multiplex. Additionally, to determine if a microdeletion was caused de novo in the test subject, the same multiplex PCR reaction is performed with DNA from the test subject's father or a fertile brother. If either the father or the brother displays the same Y-chromosome deletion, the deletion is most likely due to a polymorphic event within the Y chromosome.

Henegariu et al. established the oligo primer pairs for their PCR multiplex experiment using oligo pairs from the Y-specific part of the pY6H sequence family. Additionally, oligo pairs from Y-DNA designated sY DNA loci were prepared.

The Y-DNA sequences used in the multiplex PCR experiment were selected on the basis of their location in the neighborhood of the pY6H deletion sequence. As a positive control, Henegariu et al. incorporated the sY14 DNA sequence into every experiment. Its amplification indicates the presence of the SRY gene in the distal portion of the short arm of the Y chromosome. This area is the putative sex determining locus "TDF" of the human Y chromosome.

Lastly, the order and position of all Y-DNA loci used in the multiplex PCR experiments were confirmed by mapping to them to the sub-interval map of Ma et al., described above.

Henegariu et al. note that their PCR multiplex protocol does produce a number of experimental artifacts. For instance, as noted above, some Y chromosome loci are polymorphic. False deletion events are possible if the test subject has such a polymorphic point mutation in one of the PCR priming sites. Since the extension cycle of the PCR experiment will only produce amplification of DNA between correct primer sites, point mutations within a primer site will appear as a deletion event in the gel.

Another artifact will occur if there are multiple copies of a loci within the genome of the test subject. In this instance, the deletion of a repetitive DNA locus will only be detected if all sequence copies of this locus are deleted. If this is not the case, the remaining copies will be amplified. This possibility, however, can be obviated by use of an appropriate DNA blot experiment.

It is also noted that the PCR multiplex experiment may fail to detect a mutation event in the Y chromosome of sterile males. This may be due to point mutations or very small deletions within the genome which are not detected by the probes used.

It should be noted that the PCR multiplex combinations described by Henegariu et al. are wholly distinct from those described herein.

In 1994, *Cytogenetics and Cell Genetics* published a report of the First International Workshop on Human Y Chromosome Mapping 1994. This workshop was held on Apr. 2–5, 1994, in Cambridge, England. The workshop included discussions on the physical analysis of the Y chromosome, discussions dealing with genes which have been mapped to the pseudoautosomal region, genes mapped to the Y-specific regions of the Y chromosome, and comparative mapping and the evolution of the Y chromosome. The work of all of the above-noted authors was discussed during the workshop. The report notes that Ken McElreavey presented the analysis of five patients carrying a Yq deletion using Y chromosome-specific sequence-tagged sites (STS). It was noted that two of these patients exhibited Turner's Stigmata.

Agulnik et al. (1994) describe the isolation of a Y chromosome gene entitled SMCY. SMCY has a homologous gene on the X chromosome, entitled SMCX. SMCY was found to be well conserved on the Y chromosome in mouse, man, and even marsupials. Expression of the SMCY gene was studied by reverse transcriptase polymerase chain reaction (RT-PCR) using SMCY-specific PCR primer pair SH34Y/SH35Y, designed from the human Y genomic sequence. The studies indicate that the SMCY gene is a functional gene in man, and is widely expressed.

To map SMCY onto the human Y chromosome, the yeast artificial chromosome (YAC) set yOX of David Page was used. SMCY has been shown to be expressed in tissues other than the testis. Analysis of sex-reversed mice indicate that the sole mutant phenotype that can be correlated with the deletion of Smcy (the mouse homolog) is a post-natal failure of spermatogenesis. This indicates that Smcy plays some role in spermatogenesis.

As the above-references make clear, although great progress has been made in deciphering the secrets of the Y chromosome, there is a distinct need for a rapid and reproducible method to detect and quantify deletions on the Y chromosome which may be causative of male infertility, especially where no definitive etiology can be determined to account for the infertility.

As noted above, it is estimated that between two and eight percent of all couples are infertile. Of these infertile couples, approximately thirty to fifty percent of the cases of male fertility are categorized as being idiopathic. This relatively large number of cases of male infertility which cannot be ascribed a cause has created a strong desire on the part of researchers and practicing physicians to obtain a better understanding of the causes of male infertility.

At present, however, there are very few tools available beyond the microscopic examination of the ejaculate to diagnose causes of male infertility. For instance, macroscopic examination of the test subject's lifestyle and environment may reveal external causes of his infertility. Such causes may include environmental factors, substance abuse, and dietary insufficiencies.

However, as is made clear by the above references, normal development of the male gonads, and normal spermatogenesis is controlled, in large measure, by genes located on the Y chromosome. Furthermore, the above references also indicate that spermatogenesis is a very complicated process which is controlled by numerous genes located both on and off the Y chromosome. Importantly, it is known that normal spermatogenesis is impaired by certain mutations on the Y chromosome.

The structure of the Y chromosome includes the short arm (Yp), which is terminated by the pseudoautosomal region, and a long arm (Yq) terminated by the heterochromatic region. The centromere divides Yp from Yq. The euchromatic region of the Y chromosome spans from the pseudoautosomal region of Yp, across the centromere, and to the heterochromatic region of Yq. These terms shall be used herein as conventionally defined in the relevant art.

The euchromatic region of the Y chromosome has additionally been divided into intervals and sub-intervals by deletion mapping. The seven intervals and their respective sub-intervals provide reference points which aid in mapping nucleotide sequences to specific regions of the Y chromosome.

Of particular interest in the present invention are those genes which have been mapped to intervals five and six. These genes appear to play an important role in normal spermatogenesis. Lack of these genes, or mutations within these genes would appear to lead to severe oligospermia or complete azoospermia. Using the present multiplex PCR battery allows the existence and location of deletion mutations on the Y chromosome to be quickly and accurately determined. It is important to note, however, that spermatogenesis is an extremely complicated process. Analysis of azoospermic men, as in the above-discussed references, has shown that they often have deletions in both Yp, and Yq, as well as autosomal deletion mutations.

Because of the large number of deletion mutations which may give rise to male infertility, it is presently difficult, if not impossible, to ascribe a genetic etiology for many types of male infertility. However, by focusing upon those loci which have been shown to be linked to functional spermatogenesis, information can be gained as to the likelihood that a mutation at one of these loci is a factor in causing the observed infertility.

SUMMARY OF THE INVENTION

One embodiment of the present invention is directed to a method for assessing the integrity of a Y chromosome. The method includes the steps of first combining chromosomal DNA (either purified DNA or blood, etc.) of a test subject with a plurality of distinct oligonucleotide primer pairs capable of simultaneously priming a plurality of human chromosome loci in a multiplex PCR cocktail, wherein the plurality of human chromosome loci are selected from the following three groups of loci:

DYS240, DYS271, DYS221, KAL182, and MIC2;
DYF53S1, DYS229, DYZ1, DYS230, DAZ(3), DAZ(4), and MIC2; and
SMCY, DYS217, DYS223, DYS7, DYS237, DYS236, DYS215, MIC2.

The plurality of distinct oligonucleotide primer pairs are then amplified in a corresponding multiplex polymerase chain reaction to yield amplified chromosomal DNA fragments. The amplified chromosomal DNA fragments are then separated and compared to corresponding amplified chromosomal DNA fragments from normal male subjects to determine the integrity of the Y chromosome of the test subject.

The present invention is also drawn to kits for the detection of microdeletions and macrodeletions which occur along the Y chromosome and which are associated with human male infertility. This embodiment of the invention is directed to a kit which comprises at least one first receptacle containing at least one corresponding plurality of oligonucleotide primer pairs. The plurality of oligonucleotide primer pairs are capable of priming at least one corresponding plurality of human chromosome loci selected from the following three groups of loci:

DYS240, DYS271, DYS221, KAL182, and MIC2;
DYF53S1, DYS229, DYZ1, DYS230, DAZ(3), DAZ(4), and MIC2; and
SMCY, DYS217, DYS223, DYS7, DYS237, DYS236, DYS215, MIC2.

The kit may also include at least one second receptacle containing at least one control DNA amplimer ladder corresponding to the at least one plurality of human chromosome loci. A third receptacle containing normal human male DNA, and a fourth receptacle containing normal human female DNA may also be included in the kit. It is preferred that the kit also contains instructions for its use.

The primary goal of the present invention is to provide a method and a corresponding kit which will enable a user to rapidly and reproducibly assess the integrity of specific regions on the Y chromosome which are associated with male infertility. The present invention includes a kit which is comprised of a battery of multiplexed oligonucleotides, and which may also include conventional PCR reagents, enzymes, control amplimer ladders, and control DNA.

To rapidly determine the presence of such mutations, the present invention provides a series of multiplex PCR batteries containing oligonucleotide primer pairs which are specific for chosen regions of the human Y chromosome. More specifically still, the multiplex PCR batteries may contain primer pairs which prime the amplification of loci which have been mapped to loci on the Y chromosome known or suspected to play a part in human male fertility.

The PCR primer pairs and the Y-specific loci to be amplified are chosen based upon genetic analysis using sequence-tagged sites (STS). An STS is a short stretch of DNA specifically identified by PCR. For sake of brevity, as used in herein, STS shall refer to Y chromosome-specific STS's, unless otherwise noted. Since the STS's have already been identified by PCR, it is much easier to obtain proper PCR primers for the desired loci. Moreover, the PCR multiplex protocols have been constructed to yield efficient PCR amplification.

More than 1,000 amplifications have been performed using the multiplexes disclosed herein. These amplifications reveal that the failure rate for the multiplexes is less than 2.5%.

The multiplexes have a wide number of different utilities. Primarily, the multiplexes can be used to assess the integrity of the Y chromosome in males exhibiting azoospermia or oligospermia. The multiplexes can also be used in pediatric medicine to assess the genotype of infants with ambiguous genitalia.

The multiplexes are also useful in the field of infertility, where they can be used as a diagnostic tool for couples considering in vitro fertilization (or other related fertilization treatments). Here, the couple may want to re-think their decision to proceed if the father is shown to have one or more deletions on the Y chromosome because male offspring produced by the union will also carry the deletion. Additionally, the multiplexes can be used in pre-implantation genetic diagnosis to determine if the fertilized ovum has suffered genetic alterations.

The multiplexes also have utility as diagnostic tools for researching cancer genetics and tumorigenesis. Many of the loci amplified in the disclosed multiplexes have been shown to play an as yet undetermined role in tumorigenesis. By matching their presence or absence to an abnormal phenotype of a subject, a genotype can be ascribed to the abnormal phenotype.

The multiplexes can also be used as a quality control device to test sperm being deposited at a sperm bank.

The present invention, therefore, relates to a series of multiplexed PCR batteries for determining the presence of deletion mutations on the Y chromosome.

The present invention also relates to a kit containing the above-noted PCR multiplex reaction mixtures. The kit may include all of the reagents necessary to perform the PCR multiplex analysis. In this case, the user need only provide a sample of the test subject's blood or purified DNA. The kit may include supplies of purified water, buffers, magnesium chloride, and DNA polymerase enzymes. The kit may also contain supplies of male control DNA, female control DNA, as well as molecular weight markers and amplimer control ladders which contain DNA sequences corresponding to those loci primed by the PCR primers.

In operation, DNA from the test subject is combined separately with one or more of the PCR multiplex primer pair groupings described herein which contains positive control primer pairs derived from the X chromosome. The test subject DNA is then amplified in tandem in each of the corresponding multiplex mixes with a control PCR reaction containing control normal male DNA. The test subject's amplification products are then separated, preferably on a 3% agarose gel. The amplimer control ladder(s), and optionally male control DNA and female control DNA, are then also separated on lanes adjacent to the test subject's amplification products. The presence of a deletion event in the test subject is then quickly determined by comparing the test subject's lane(s) to that of the amplimer control ladder(s). Deletion mutations within the test subject will appear as an omitted band in the test subject's gel electrophoresis lane.

The present invention provides a number of both clinical and pure research applications. In the clinical setting, the present multiplex PCR battery can be used to predict infertility in males. Additionally, by identifying the location of deletion mutations, the present invention provides the first step in the restoration of fertility by gene therapy. On the reverse of the same coin, by identifying those loci necessary for spermatogenesis, the present invention may be used to direct specific mutations designed to result in male infertility as a form of contraception.

From a research perspective, the present invention can be used to gain a better understanding of the role of the Y chromosome, and the genes thereon. Additionally, the present invention may be used to predict phenotypes resulting from a given Y chromosome deletion mutation.

In view of the above, it is a principal aim of the present invention to provide a Y-chromosome-specific multiplex PCR analysis method to determine, rapidly and reproducibly, the integrity of a Y-chromosome.

Additionally, it is an aim of the present invention to provide a kit containing reagents needed to perform the method described herein.

These and other aims and functions of the presently claimed invention will become clear upon a complete reading of the DETAILED DESCRIPTION OF THE INVENTION and attached Claims.

DEFINITIONS

Figure 1:
FIG. 1 is a photograph of an electrophoresis gel depicting two parallel duplicative runs of the 5-2 multiplex Y-deletion detection battery according to the present invention.

The following definitions are intended to assist in providing a clear and consistent understanding of the scope and detail of the terms:

Allelic ladder: a standard size marker consisting of amplified alleles from the locus.

Allele: a genetic variation associated with a segment of DNA, i.e., one of two or more alternate forms of a DNA sequence occupying the same locus.

Amplimer (control) ladder: a standard size marker consisting of amplified fragments from a plurality of different loci. Analogous to an allelic ladder, above.

Biochemical nomenclature: standard biochemical nomenclature is used herein in which the nucleotide bases are designated as adenine (A); thymine (I); guanine (G); and cytosine (C). Corresponding nucleotides are, for example, deoxyguanosine-5'-triphosphate (dGTP).

DNA polymorphism: the condition in which two or more different nucleotide sequences coexist in the same interbreeding population in a DNA sequence.

Locus (or genetic locus): a specific position on a chromosome. Alleles of a locus are located at identical sites on homologous chromosomes.

Locus-specific primer: a primer that specifically hybridizes with a portion of the stated locus or its complementary strand, at least for one allele of the locus, and does not hybridize efficiently with other DNA sequences under the conditions used in the Polymerase chain reaction (PCR): a technique in which cycles of denaturation, annealing with primer, and extension with DNA polymerase are used to amplify the number of copies of a target DNA sequence by $>10^6$ times. The PCR process for amplifying nucleic acids is covered by U.S. Pat. Nos. 4,683,195, and 4,683,202, which are incorporated herein by reference for a description of the process. A multiplex PCR is an analogous technique in which two or more distinct target DNA sequences are amplified simultaneously within the same sample.

Primary reaction: initial reaction using the purified human genomic DNA as template for the PCR.

Primers: two single-stranded oligonucleotides or DNA fragments which hybridize with opposing strands of a locus such that the 3' termini of the primers are in closest proximity.

Primer pair: two primers including primer 1 that hybridizes to a single strand at one end of the DNA sequence to be amplified and primer 2 that hybridizes with the other end on the complementary strand of the DNA sequence to be amplified. Also referred to as the right and left primers.

Primer site: the area of the target DNA to which a primer hybridizes.

Secondary reaction: reamplification with the same or different primer pair using a dilution of the primary reaction as template for the PCR.

DETAILED DESCRIPTION OF THE INVENTION

Construction of the Multiplex System

Prior to constructing the multiplex system, an appropriate set of loci, primers, and amplification protocols must be selected such that amplification generates fragments of the various amplified loci which do not overlap in size or, when such overlap occurs, fragments representing different loci are detectable by separate means. It is preferred that the amplified fragments do not overlap in gel electrophoresis.

In addition, the selected loci should be also compatible for use with a single amplification protocol so that specific deletion events may be corroborated. Furthermore, an internal positive control is preferably built into the multiplexes to provide a positive control amplification in patient, normal male, and normal female samples. The specific combinations of loci described herein are unique to this application. Other combinations of loci have been rejected for the above reasons, or because, in combination, one or more of the loci do not produce adequate product yield, or fragments which do not represent authentic alleles are produced in the reaction.

Successful combinations are generated by trial and error of STS combinations and by adjustment of primer concentrations to identify an equilibrium in which all included loci will be successfully amplified. In addition, unique STS primers have been generated from direct sequencing of amplimers as well as from one-direction extension in regions which flank deletion breakpoints in infertile patients. These STS's have been mapped to specific loci and incorporated into the subject multiplex Y-deletion detection battery.

Of particular importance in the multiplex system is the size range of amplified loci produced from the individual loci which will be analyzed together. For ease of analysis with current technologies, systems which can be detected by amplification of fragments smaller than 500 bases were preferably selected or produced from generated sequencing reactions.

Additionally, for ease of analysis, STS's were chosen which prime amplification of loci having sufficiently distinct molecular weights from each other to be cleanly and unambiguously separated by electrophoresis on agarose gels. This makes the detection of deletion events simple and apparent. Interpretation of the results of a given analysis therefore inspires confidence due to the simplicity of the analysis.

The specific STS's, Y-chromosome loci, and the size of the amplified products employed in the present invention are shown in Table 1:

TABLE 1

MULTIPLEX BATTERIES

| MULTIPLEX NAME | LOCI | STS | SIZE (B.P.) |
|---|---|---|---|
| 5-2 | DYS240 | SY157 | 285 |
|  | DYS271 | SY81 | 209 |
|  | DYS221 | SY130 | 173 |
|  | KAL182 | SY182 | 125 |
|  | MIC2 | SY4 | 80 |
| 7-1 | DYF53S1 | SY155 | 349 |
|  | DYS229 | SY141 | 290 |
|  | DYZ1 | SY160 | 236 |
|  | DYS230 | SY142 | 196 |
|  | DAZ(3) | SY231 | 149 |
|  | DAZ(4) | SY202 | 121 |
|  | MIC2 | SY4 | 80 |
| 8-2 | SMCY | SYPR3 | 370 |
|  | DYS217 | SY126 | 323 |
|  | DYS223 | SY133 | 177 |
|  | DYS7 | SY132 | 159 |
|  | DYS237 | SY153 | 139 |
|  | DYS236 | SY152 | 125 |
|  | DYS215 | SY124 | 109 |
|  | MIC2 | SY4 | 80 |

Methodology of Performing the Analysis

To perform the present method, first, blood is drawn from the individual to be tested. This is done in conventional fashion, normally in EDTA or acid citrate. The blood is then processed to isolate the DNA contained therein. This may also be done using any conventional method, such as using Promega Corporation's Wizard® (Madison, Wis.), or by extraction using standard phenol chloroform methods. A minimum amount of about 100 ng DNA is needed per test subject. It is recommended that residual blood or DNA be stored at −20° C. for future use if deletions are detected. Approximately 100 ng of test subject and control DNA is used for each reaction tube.

For each multiplex PCR amplification, the following preferred procedure is preferably followed:

Into an amplification container, pipette 100 ng of test subject DNA into a total template volume of 10 microliter of nanopure water, followed by 40 microliters of a selected multiplex mixture (8-1 or 8-2 as shown in Table 1). The tube should then be agitated, preferably using a vortex. A suitable amount of Taq DNA polymerase is then added to the tube, and the tube is agitated and followed by pulse centrifugation.

This same procedure is then repeated in parallel fashion using separate tubes for: 1) the control normal male DNA which, upon amplification, will serve as a normal standard amplification and deletion control; and 2) the control normal female DNA.

The above procedure is repeated for each of the multiplexes which is performed. Thus, an exhaustive multiplex Y-deletion detection analysis might include, for each multiplex shown in Table 1, a tube for the test subject's DNA, and a corresponding tube of control amplimer ladder DNA containing normal fertile male DNA, each tube containing all components needed for optimal amplification. Optionally, for each of multiplex, a negative (human male contamination) control tube containing 100 ng human female DNA plus the respective multiplex mix may also be tested. As an added precaution against extraneous contamination, 10 microliters of nanopure water in yet another tube might also be tested as a template control.

All components should be kept on ice during preparation. For high throughput analyses, it is recommended that patients to be tested be batched in groups of 5 to 10. If this is done, a set of controls may be only necessary for the first patient in a given "batched" PCR amplification. Blood can be stored for up to four weeks at 4° C. and DNA can be stored indefinitely at −20° C.

To amplify, one drop of sterile mineral oil is added to each tube. The tubes are then closed and placed on a licensed thermocycler and amplified as follows: initial denaturation: 95° C. for 2.5 minutes; denaturation: 95° C. for one minute; annealing: 61° C. for 1 minute; extension: 72° C. for 1 minute. The amplification protocol should be repeated for thirty-five cycles.

After amplification, the samples are held at 4° C. The amplification products are separated on a standard 3% agarose gel (for instance "METAPHORE" or "NUSEIVE" brands) using conventional and well-known electrophoretic procedures. After electrophoresis is complete, the gel is stained with ethidium bromide according to standard protocols, visualized on a UV light box, and photographed. The photographs are then analyzed for the presence of deletion events.

The preferred oligonucleotide locus-specific primer sequences for use in the present invention, and the preferred primer concentration (concentration per primer) in the amplification reaction are listed in Table 2. It must be noted that the primer concentrations listed in Table 2 are the most preferred concentrations. In general, primer concentrations falling within the range of from about 5 to about 100 pM are ideal.

TABLE 2

Preferred Oligonucleotide Primer Sequences

| MULTILPEX LOCI | PRIMER 1 | PRIMER 2 | PRIMER CONC'TRA-TION, PER PRIMER, pM |
|---|---|---|---|
| 5-2 | | | |
| DYS240 | Seq. Id. No: 1 | Seq. Id. No: 2 | 53.0 |
| DYS271 | Seq. Id. No: 3 | Seq. Id. No: 4 | 40.5 |
| DYS221 | Seq. Id. No: 5 | Seq. Id. No: 6 | 53.0 |
| KAL182 | Seq. Id. No: 7 | Seq. Id. No: 8 | 27.0 |
| MIC2 | Seq. Id. No: 9 | Seq. Id. No: 10 | 26.5 |
| 7-1 | | | |
| DYF53S1 | Seq. Id. No: 11 | Seq. Id. No: 12 | 18.5 |
| DYS229 | Seq. Id. No: 13 | Seq. Id. No: 14 | 7.0 |
| DYZ1 | Seq. Id. No: 15 | Seq. Id. No: 16 | 27.5 |
| DYS230 | Seq. Id. No: 17 | Seq. Id. No: 18 | 9.5 |
| DAZ(3) | Seq. Id. No: 19 | Seq. Id. No: 20 | 10.0 |
| DAZ(4) | Seq. Id. No: 21 | Seq. Id. No: 22 | 100.0 |
| MIC2 | Seq. Id. No: 23 | Seq. Id. No: 24 | 27.5 |
| 8-2 | | | |
| SMCY | Seq. I.D. No. 25 | Seq. I.D. No. 26 | 12.5 |
| DYS217 | Seq. I.D. No. 27 | Seq. I.D. No. 28 | 27.5 |
| DYS223 | Seq. I.D. No. 29 | Seq. I.D. No. 30 | 58.0 |
| DYS7 | Seq. I.D. No. 31 | Seq. I.D. No. 32 | 15.5 |
| DYS237 | Seq. I.D. No. 33 | Seq. I.D. No. 34 | 20.0 |
| DYS236 | Seq. I.D. No. 35 | Seq. I.D. No. 36 | 10.0 |
| DYS215 | Seq. I.D. No. 37 | Seq. I.D. No. 38 | 26.5 |
| MIC2 | Seq. I.D. No. 39 | Seq. I.D. No. 40 | 30.0 |

The Test Kit

The kit of the present invention is designed to detect small Y chromosome-linked deletions which are associated with the various types of human male infertility in a reliable and reproducible manner with built-in internal controls. In the preferred embodiment of the kit, the kit includes all of the necessary reagents and containers to successfully practice the method, while simultaneously minimizing the possibility of both human errors and experimental errors.

In the most preferred embodiment, the kit includes the STS oligonucleotide primer pairs listed in Table 2, packaged together in a ready to use, user-friendly format which includes the following items:

(a) Ten multiplex mixes which contain oligonucleotide pairs capable of priming amplification of the loci detailed in Table 1, reaction buffer, magnesium, dNTP's, and sterile water combined together at pre-optimized, PCR-suitable concentrations and ratios. Preferably, sufficient multiplex mix is provided to allow the end user to assay ten patients and their corresponding controls. The ten multiplex mixes are placed in separate containers, and labeled accordingly.

(b) Ten control amplimer ladders to be used as gel electrophoresis molecular weight control markers. The ten control amplimer ladders correspond with the ten multiplex mixes described in (a) above. The ten control amplimer ladders are placed in separate containers, and labeled accordingly. In practice, each multiplex is separated and resolved on an agarose gel with its respective control male amplification and amplimer ladder being electrophoresed on a parallel lane for ease of size and quality comparison.

(c) Control normal male DNA. (Promega Part #G147, Madison, Wis.).

(d) Control normal female DNA. (Promega Part #G152, Madison, Wis.).

(e) Nanopure water.

The kit may also include a number of optional items to increase the convenience of the kit. Included among these additional optional items are Taq DNA polymerase, sterile mineral oil, a plurality of pre-sterilized 0.5 ml microfuge tubes, molecular weight control markers (for instance PGEM Promega Part #DG17A), and electrophoresis gel loading dye (for instance Promega Part #DV433A). All of the elements of the kit are then packaged within a single, user-friendly container along with instructions on how to properly use the kit.

As noted above, the preferred individual oligonucleotide locus-specific primer pairs for the multiplexes and the preferred primer concentrations are listed in Table 2.

Advantages of the Kit

The kit provides an easy and simple method for determining the presence of deletion mutations on the Y chromosome in areas which have been tied to abnormal spermatogenesis. The various STS's combined in each multiplex were selected: 1) because of the absence of contaminating X-chromosome, autosome, or duplicated Y-linked sequences; 2) because of their compatibility with one another within a multiplexed reaction; 3) because the deletions associated with specific amplimers have not been shown to be associated with a statistically significant sampling of fertile males; and 4) because they amplify a DNA product which is sufficiently different in size from the other products amplified within the multiplex such that the amplified fragments separate cleanly on conventional agarose gels. This makes analyzing the gels for deletion mutations quick and simple, and minimizes the risk of false positive deletion events or experimental artifacts masking the presence of a deletion event (i.e. a false negative). A special effort has been made to provide unique STS's from selected regions in which a high frequency of deletions associated with infertility (minimally, azoospermia and oligospermia) is observed.

Of paramount importance is that the kit be "user friendly," and extremely simple in use. This minimizes the chance of human error, while simultaneously increasing the accuracy and reproducibility of the assay. This is accomplished by combining the necessary reagents and containers therefor in a single kit, along with concise instructions for its use. In this manner, the present invention allows for the assay of the Y chromosome of a male test subject for deletion mutations in a matter of hours.

Moreover, because the test kit employs the PCR methodology, a widely accepted and respected experimental technique, its reliability and acceptance by those of skill in the art is assured.

EXPERIMENTAL EXAMPLES

The following examples are provided for illustrative purposes only. It is understood that the following examples do not limit the invention claimed herein in any manner.

Example 1

Multiplex 5-2

FIG. 1 depicts a duplicative parallel electrophoresis gel of multiplex 5-2 as described in Table 1, above. The alleles shown in this drawing figure are, from top to bottom: DYS240, DYS271, DYS221, KAL182, and MIC2;

To generate this gel, the protocol described above was employed, using normal male human blood as a DNA source. After DNA preparation by conventional and well known means, a mixture of the sample DNA and the preferred primers for multiplex 8-1 in the preferred concentrations described in Table 2 was assembled in a suitable PCR cocktail solution. The solution was then placed in a licensed thermocycler and amplified as follows: initial denaturation: 95° C. for 2.5 minutes; denaturation: 95° C. for one minute; annealing: 61° C. for 1 minute; extension: 72° C. for 1 minute. The cycle was repeated thirty-five times.

The resultant amplified fragments were then loaded onto a standard 3% agarose gel, electrophoresed in standard fashion, stained with ethidium bromide, visualized under an ultraviolet light source and photographed. The resultant image is depicted in FIG. 1.

Example 2

Multiplex 7-1

Figure 2:
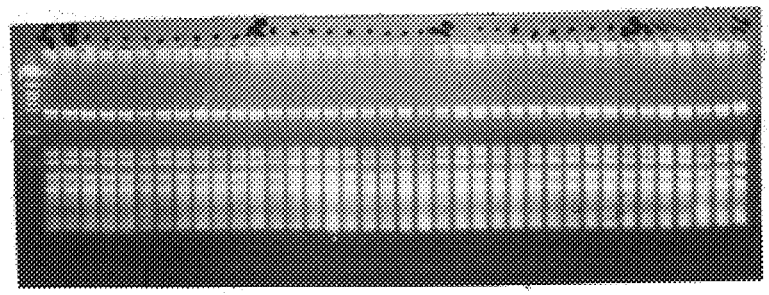
FIG. 2 is a photograph of an electrophoresis gel depicting a plurality of duplicative runs of the 7-1 multiplex Y-deletion detection battery of the present invention.

The same protocol as described in Example 1 was used, with the exception that Example 2 depicts an electrophoresis gel of multiplex 7-1 as described in Table 1, above. The preferred primers and concentrations as listed in Table 2 for multiplex 7-1 were utilized. The sample DNA was isolated from normal human male blood. The results of this Example are depicted in FIG. 2. As depicted in FIG. 2, the alleles for multiplex 7-1, from top to bottom in both lanes, are: DYF53S1, DYS229, DYZ1, DYS230, DAZ(3), DAZ(4), and MIC2;

Example 3

Multiplex 8-2

Figure 3:
FIG. 3 is a photograph of an electrophoresis gel depicting two parallel duplicative runs of the 8-2 multiplex Y-deletion detection battery of the present invention.

Here, the same protocol as described in Example 1 was used, with the exception that Example 3 depicts an electrophoresis gel of multiplex 8-2 as described in Table 1, above. The preferred primers and concentrations as listed in Table 2 for multiplex 8-2 were utilized. The sample DNA was isolated from normal human male blood. The results of this Example are depicted in FIG. 3. As depicted in FIG. 3, the alleles for multiplex 8-2, from top to bottom in both lanes, are: SMCY, DYS217, DYS223, DYS7, DYS237, DYS236, DYS215, and MIC2.

The present invention is not limited to the embodiments specifically enumerated above, but encompasses all such forms and variations thereof as are encompassed by the following claims.

BIBLIOGRAPHY

Ma, K., Sharkey, A., Kirsch, S., Vogt, P., Keil, R., Hargreave, T. B., McBeath, S., and Chandley, A. C. (1992) *Towards the molecular localisation of the AZF locus: mapping of microdeletions in azoospermic men within 14 subintervals of interval 6 of the human Y chromosome.* H. Mol. Gen. 1, 29–33.

Ma, K., Inglis, J. D., Sharkey, A., Bickmore, W. A., Hill, R. E., Prosser, E. J., Speed, R. M., Thomson, E. J., Jobling, M., Taylor, K., Wolfe, J., Cooke, H. J., Hargreave, T. B., and Chandley, A. C., (1993) *A Y Chromosome Gene Family with RNA-Binding Protein Homology: Candidates for the Azoospermia Factor AZF Controlling Human Spermatogenesis.* Cell 75, 1287–1295.

Agoulnik, A. I., Mitchell, M. J., Lerner, J. L., Woods, D. R., and Bishop, C. E. (1994) *A mouse Y chromosome gene encoded by a region essential for spermatogenesis and expression of male-specific minor histocompatibility antigens.* H. Mol. Gen. 3, 873–878.

Affara, N. A., Lau, Y. -F. C., Briggs, H., Davey, P., Jones, M. H., Khwaja, O., Mitchell, M., and Sargent, C. (1994) *Report of the First International Workshop on Y Chromosome Mapping 1994.* Cytogenet Cell Genet 67, 359–402.

Nagafuchi, S., Namiki, M., Nakahori, Y., Kondoh, N., Okuyama, A., and Nakagome, Y. (1993) *A Minute Deletion Of The Y Chromosome In Men With Azoospermia.* The J. of Urol. 150, 1155–1157.

Kobayashi, K., Mizuno, K., Hida, A., Komaki, R., Tomita, K., Matsishita, I., Namiki, M., Iwamoto, T., Tamura, S., Minowada, S., Nakahori, Y., and Nakagome, Y. (1994) *PCR analysis of the Y chromosome long arm in azoospermic patients: evidence for a second locus required for spermatogenesis.* H. Mol. Gen. 3, 1965–1967.

Henegariu, O., Hirschmann, P., Kilian, K., Kirsch, S., Lengauet, C., Maiwald, R., Mielke, K., and Vogt, P. (1994) *Rapid screening of the Y chromosome in idiopathic sterile men, diagnostic for deletions in AZF, a genetic Y factor expressed during spermatogenesis.* ANDROLOGIA 26, 97–106.

Chandley, A. C. and Cooke, H. J. (1994) *Human male fertility-Y-linked genes and spermatogenesis.* H. Mol. Gen. 3, 1449–1452.

What is claimed is:

1. A method for detecting deletions in a Y chromosome which are indicative of male infertility comprising:
   (a) combining a plurality of distinct oligonucleotide primer pairs capable of priming a corresponding plurality of human X and Y chromosome loci selected from the group consisting of:
      DYS240, DYS271, DYS221, KAL182, and MIC2;
      DYF53S1, DYS229, DYZ1, DYS230, DAZ(3), DAZ(4), and MIC2; and
      SMCY, DYS217, DYS223, DYS7, DYS237, DYS236, DYS215, MIC2;
   with isolated genomic DNA of a test subject; then
   (b) amplifying the plurality of distinct oligonucleotide primer pairs by a corresponding multiplex polymerase chain reaction to yield locus-specific amplified chromosomal DNA fragments; then
   (c) separating the amplified chromosomal DNA fragments; and then
   (d) comparing the amplified chromosomal DNA fragments to corresponding amplified chromosomal DNA fragments from normal male subjects, whereby deletions in the Y chromosome of the test subject are detected.

2. The method according to claim 1, wherein in step (a) the genomic DNA of the test subject is combined with at least one plurality of distinct oligonucleotide primer pairs selected from the group consisting of SEQ. ID. NOS: 1–10, SEQ. ID. NOS: 11–24, and SEQ. ID. NOS: 25–40.

3. The method according to claim 1, wherein in step (a) the plurality of distinct oligonucleotide primer pairs is combined with genomic DNA of a human test subject.

4. The method according to claim 3, wherein in step (a) the plurality of distinct oligonucleotide primer pairs is combined with genomic DNA of a phenotypically male human test subject.

5. The method according to claim 3, wherein in step (a) the plurality of distinct oligonucleotide primer pairs is combined with genomic DNA of a human test subject of phenotypically ambiguous sexuality.

6. The method according to claim 3, wherein in step (a) the plurality of distinct oligonucleotide primer pairs is combined with genomic DNA of a phenotypically female human test subject.

7. The method according to claim 1, wherein in step (c), the amplified chromosomal DNA fragments are separated by agarose or polyacrylamide gel electrophoresis.

8. The method according to claim 1, wherein in step (b) the plurality of distinct oligonucleotide primer pairs amplified by at least one corresponding multiplex polymerase chain reaction are amplified by subjecting the corresponding multiplex polymerase chain reaction to an initial denaturation at about 95° C. for about 2.5 minutes, and then cycling through 25 to 35 cycles of denaturation at about 95° C. for about 1 minute, annealing at about 61° C. for about 1 minute, and extension at about 72° C. for about 1 minute.

9. A kit for detecting deletion mutations on a Y chromosome which are indicative of male infertility comprising in combination:
   at least one first receptacle containing at least one corresponding plurality of locus-specific oligonucleotide primer pairs, said at least one corresponding plurality of oligonucleotide primer pairs capable of specifically priming at least one corresponding plurality of human X and Y chromosome loci selected from the group consisting of:
      DYS240, DYS271, DYS221, KAL182, and MIC2;
      DYF53S1, DYS229, DYZ1, DYS230, DAZ(3), DAZ(4), and MIC2; and
      SMCY, DYS217, DYS223, DYS7, DYS237, DYS236, DYS215, MIC2;
   at least one second receptacle containing at least one control DNA amplimer ladder corresponding to said at least one plurality of human X and Y chromosome loci; and
   instructions for use.

10. The kit according to claim 9, wherein said at least one corresponding plurality of oligonucleotide primer pairs is selected from the group consisting of: SEQ. ID. NOS: 1 through 10, SEQ. ID. NOS: 11–24, and SEQ. ID. NOS: 25–40.

11. The kit according to claim 9, wherein said at least one corresponding plurality of oligonucleotide primer pairs is SEQ. ID. NOS: 1 through 10, SEQ. ID. NOS: 11–24, and SEQ. ID. NOS: 25–40.

12. The kit according to claim 9, further comprising a supply of nanopure water, a supply of PCR-suitable buffer, a supply of PCR-suitable magnesium, and a supply of PCR-suitable dNTP's.

13. The kit according to claim 12, further comprising at least one third receptacle, wherein said supplies of nanopure water, PCR-suitable buffer, PCR-suitable magnesium, and PCR-suitable dNTP's are combined together at PCR-suitable concentrations and disposed therein.

14. The kit according to claim 9, wherein said at least one corresponding plurality of oligonucleotide primer pairs and said at least one control DNA amplimer ladder are contained respectively in said at least one first receptacle and said at least one second receptacle, in combination with PCR-suitable concentrations of nanopure water, PCR-suitable buffer, PCR-suitable magnesium, and PCR-suitable dNTP's.

15. The kit according to claim 9, further comprising a plurality of pre-sterilized microfuge receptacles.

16. The kit according to claim 9, further comprising a supply of Taq DNA polymerase.

17. The kit according to claim 9, further comprising a supply of sterile mineral oil.

18. The kit according to claim 17, further comprising a supply of molecular weight DNA control markers.

19. The kit according to claim 9, further comprising a supply of gel electrophoresis loading dye.

20. The kit according to claim 9, further comprising a supply of normal human female DNA, and a supply of normal human male DNA.

21. A kit for detecting deletion mutations on a Y chromosome which are indicative of male infertility comprising in combination:
   at least one first receptacle containing at least one corresponding plurality of locus-specific oligonucleotide primer pairs, said at least one corresponding plurality of oligonucleotide primer pairs capable of specifically priming at least one plurality of human X and Y chromosome loci selected from the group consisting of:
DYS240, DYS271, DYS221, KAL182, and MIC2;
DYF53S1, DYS229, DYZ1, DYS230, DAZ(3), DAZ(4), and MIC2; and
SMCY, DYS217, DYS223, DYS7, DYS237, DYS236, DYS215, MIC2, in combination with PCR-suitable concentrations of nanopure water, PCR-suitable buffer, PCR-suitable magnesium, and PCR-suitable dNTP's;

at least one second receptacle containing at least one control DNA amplimer ladder corresponding to said at least one plurality of human chromosome loci, in combination with PCR-suitable concentrations of nanopure water, PCR-suitable buffer, PCR-suitable magnesium, and PCR-suitable dNTP's;

a plurality of pre-sterilized microfuge receptacles;

a supply of Taq DNA polymerase;

a supply of sterile mineral oil;

a supply of molecular weight DNA control markers;

a supply of gel electrophoresis loading dye;

a supply of normal human female DNA;

a supply of normal human male DNA; and instruction for use.

* * * * *

UNITED STATES PATENT AND TRADEMARK OFFICE
CERTIFICATE OF CORRECTION

PATENT NO. : 5,840,549
DATED : November 24, 1998
INVENTOR(S) : Marijo Kent First, Ariege Muallem It is certified that error appears in the above-identified patent and that said Letters Patent is hereby corrected as shown below:

In Column 9, line 43, after the word thymine, delete "(I)" and insert --(T)--.

In Column 9, line 57, after the word the, insert --amplification method.--

Signed and Sealed this

Thirteenth Day of April, 1999

Attest:

Q. TODD DICKINSON

*Attesting Officer*  *Acting Commissioner of Patents and Trademarks*